US006923780B2

(12) United States Patent
Price et al.

(10) Patent No.: US 6,923,780 B2
(45) Date of Patent: Aug. 2, 2005

(54) FOOT ORTHOSIS WITH DETACHABLE SKID SOLE PLATE

(76) Inventors: Mary Price, 13804 Sumac Pl., Tampa, FL (US) 33625; Steve Price, 13804 Sumac Pl., Tampa, FL (US) 33625

( * ) Notice: Subject to any disclaimer, the term of this patent is extended or adjusted under 35 U.S.C. 154(b) by 55 days.

(21) Appl. No.: 10/434,640

(22) Filed: May 9, 2003

(65) Prior Publication Data

US 2004/0082895 A1 Apr. 29, 2004

(51) Int. Cl.[7] ................................................. A61F 5/00
(52) U.S. Cl. ............................................ 602/27; 602/5
(58) Field of Search ............................. 36/59, 62, 66; 602/5, 27, 28, 29, 65, 6; 2/24, 62, 22

(56) References Cited

U.S. PATENT DOCUMENTS

| 4,177,583 | A | * | 12/1979 | Chapman | 36/77 R |
|---|---|---|---|---|---|
| 5,324,219 | A | * | 6/1994 | Beltrani et al. | 441/64 |
| 5,569,173 | A | * | 10/1996 | Varn | 602/27 |
| 5,569,174 | A | * | 10/1996 | Varn | 602/27 |
| 5,609,570 | A | * | 3/1997 | Lamont | 602/65 |
| 5,944,679 | A | * | 8/1999 | DeToro | 602/27 |
| 6,090,059 | A | * | 7/2000 | Wasserman et al. | 602/27 |
| 6,277,087 | B1 | * | 8/2001 | Hess et al. | 602/27 |
| 6,302,858 | B1 | * | 10/2001 | DeToro et al. | 602/5 |
| 6,464,659 | B1 | * | 10/2002 | DeToro et al. | 602/27 |
| 6,467,198 | B1 | * | 10/2002 | James | 36/115 |
| 6,478,762 | B1 | * | 11/2002 | Varn | 602/27 |

* cited by examiner

*Primary Examiner*—Henry Bennett
*Assistant Examiner*—Dinnatia Doster-Greene
(74) *Attorney, Agent, or Firm*—Adam H. Jacobs

(57) ABSTRACT

A foot orthosis includes a generally "L"-shaped splint having a generally upright leg-engaging section and a forwardly-extending foot support section with at least a portion of the splint being substantially transparent. A generally flexible foot receiving and retaining boot is removably mounted on the splint for releasably securing a foot on the splint, and a tongue-receiving pocket is mounted on one of the splint and the boot, the tongue-receiving pocket having at least one opening and a tongue retaining section therein. A generally planar skid pad includes an attached tongue section projecting from the skid pad, and the tongue section of the skid pad is insertable into the tongue-receiving pocket such that the tongue is releasably secured in the tongue-receiving pocket and the skid pad is thus releasably secured on one of the splint and the boot.

16 Claims, 4 Drawing Sheets

FOOT ORTHOSIS WITH DETACHABLE SKID SOLE PLATE

BACKGROUND OF THE INVENTION

1. Technical Field

The present invention relates to orthotic devices for feet and, more particularly, to a foot orthosis having a generally L-shaped lower leg and foot support splint having a transparent heel section permitting viewing of the heel and a skid pad having a tongue for insertion into a tongue-receiving pocket on the underside of the boot for releasably securing the skid pad on the boot.

2. Description of the Prior Art

Numerous types of devices intended to immobilize the lower leg and foot of a human patient are available. Examples of simple devices such as casts or splints are well known in the art. Other more recent devices provide certain limited immobilization and protection benefits but, because of their design, do not provide protection against immobilization problems such as decubitus ulcers (pressure sores).

Accordingly, there is a need for a multi-function orthosis for the foot, heel, ankle and lower leg which provides three-dimensional immobilization and protection benefits, minimizes the risk of pressure sores on the heel and posterior portion of the lower leg, provides a range of therapeutic pressures and positions for the foot, yet still allows ambulation of the patient without removal of the device. An important feature of such devices found in the prior art is the inclusion of a frictional skid pad or sole plate which is attached to the underside of the orthotic device and helps to prevent slipping. Each of the devices in the prior art that include such a skid pad attaches the skid pad to the orthotic device by hardware such as a bolt and nut arrangement or the like which extends from the orthotic device for the skid pad to be mounted thereto. A major disadvantage of this design, however, is that the hardware is directly underneath the patient's foot and this often impedes walking on the injured extremity, which can jeopardize the rehabilitation of the injury. Furthermore, the risk of walking is increased by many of the devices of the prior art due to the invasive hardware on the underside of the devices, which increases the chance for injury and thus increases the potential liability of the care giver, which unfortunately has become a prime consideration in the operation of such facilities. There is therefore a need for a foot and ankle orthotic device which substantially eliminates the underfoot hardware of the prior art.

Another problem encountered in the prior art is that when the orthotic devices include a toe plate, which is a support plate mounted forwardly on the orthotic device beneath the toes, the adjustment mechanism for the toe plate is often the same type of invasive hardware as that found in connection with the skid pad mounting hardware. When the toe plate is connected by a nut and bolt arrangement as is found on the vast majority of prior art devices, the nurse or care provider must unscrew the nut to adjust the toe plate, which can cause further aggravation to the injured extremity, particularly if the nut has been tightened previously and tools are needed to perform the adjustment. There is therefore a need for a toe plate mounting and adjustment arrangement which will substantially eliminate the underfoot hardware of the prior art.

Thus, an object of the present invention is to provide an improved foot orthosis.

Another object of the present invention is to provide an improved foot orthosis which substantially eliminates the dangers inherent in the prior art caused by the nut and bolt combination used for securement of the skid pad to the orthotic device.

Another object of the present invention is to provide an improved foot orthosis which substantially eliminates the dangers inherent in the prior art caused by the hardware mounting of the toe plate on the orthotic device.

Another object of the present invention is to provide an improved foot orthosis which includes a skid pad having a projecting tongue section which fits within and is releasably secured by a tongue-receiving pocket mounted on the underside of the foot orthosis.

Another object of the present invention is to provide an improved foot orthosis which includes a toe plate having a tongue portion which is inserted into and releasably secured within the pocket thereby eliminating the invasive hardware of the prior art.

Finally, an object of the present invention is to provide an improved foot orthosis which is relatively simple and durable in construction and is safe and effective in use.

SUMMARY OF THE INVENTION

The present invention provides a foot orthosis which includes a generally "L"-shaped splint having a generally upright leg-engaging section and a forwardly-extending foot support section with at least a portion of the splint being substantially transparent. A flexible foot receiving and retaining boot is removably mounted on the splint for releasably securing a foot on the splint, and a tongue-receiving pocket is mounted on one of the splint and the boot, the tongue-receiving pocket having at least one opening and a tongue retaining section therein. A generally planar skid pad includes an attached tongue section projecting from the skid pad, and the tongue section of the skid pad is insertable into the tongue-receiving pocket such that the tongue is releasably secured in the tongue-receiving pocket and the skid pad is releasably secured on one of the splint and the boot.

The combination of the tongue and pocket substantially eliminates the need for invasive or potentially injurious hardware to be mounted on the underside of the foot orthosis of the present invention. Furthermore, as the skid pad can be removed or replaced by merely sliding the tongue out of and into the pocket, movement of the foot orthosis and hence the injured extremity is greatly reduced, thus preventing further injury to the extremity. Finally, the pocket and/or tongue may be modified to include a fastening material such as hook and loop fasteners or the like to ensure that the skid pad remains in place on the foot orthosis while not adding potentially damaging hardware to the device. It is thus seen that the present invention provides a substantial improvement over those devices found in the prior art.

DESCRIPTION OF THE PREFERRED EMBODIMENT

Figure 1:
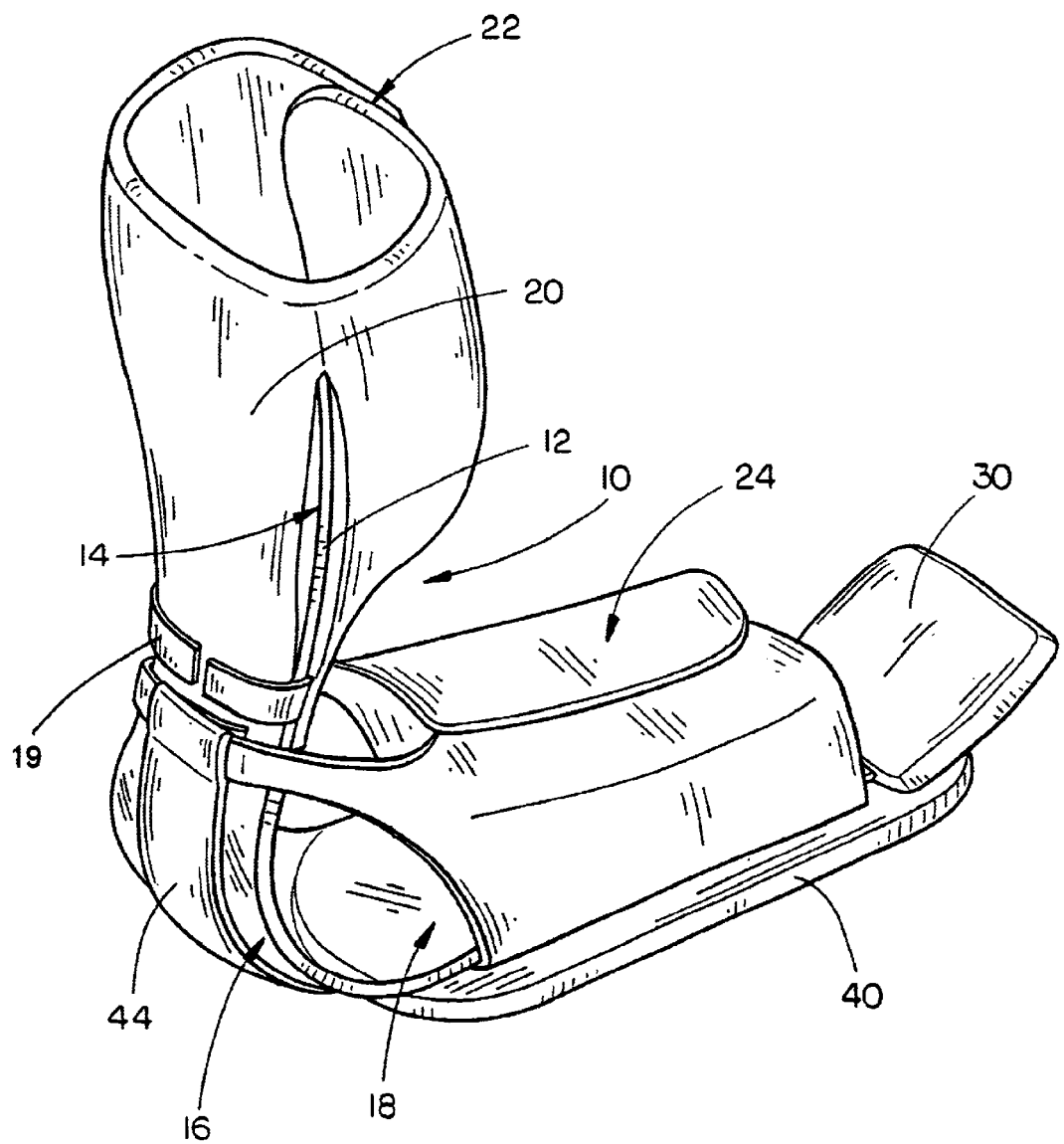
FIG. 1 is a perspective view of the present invention.
Figure 2:
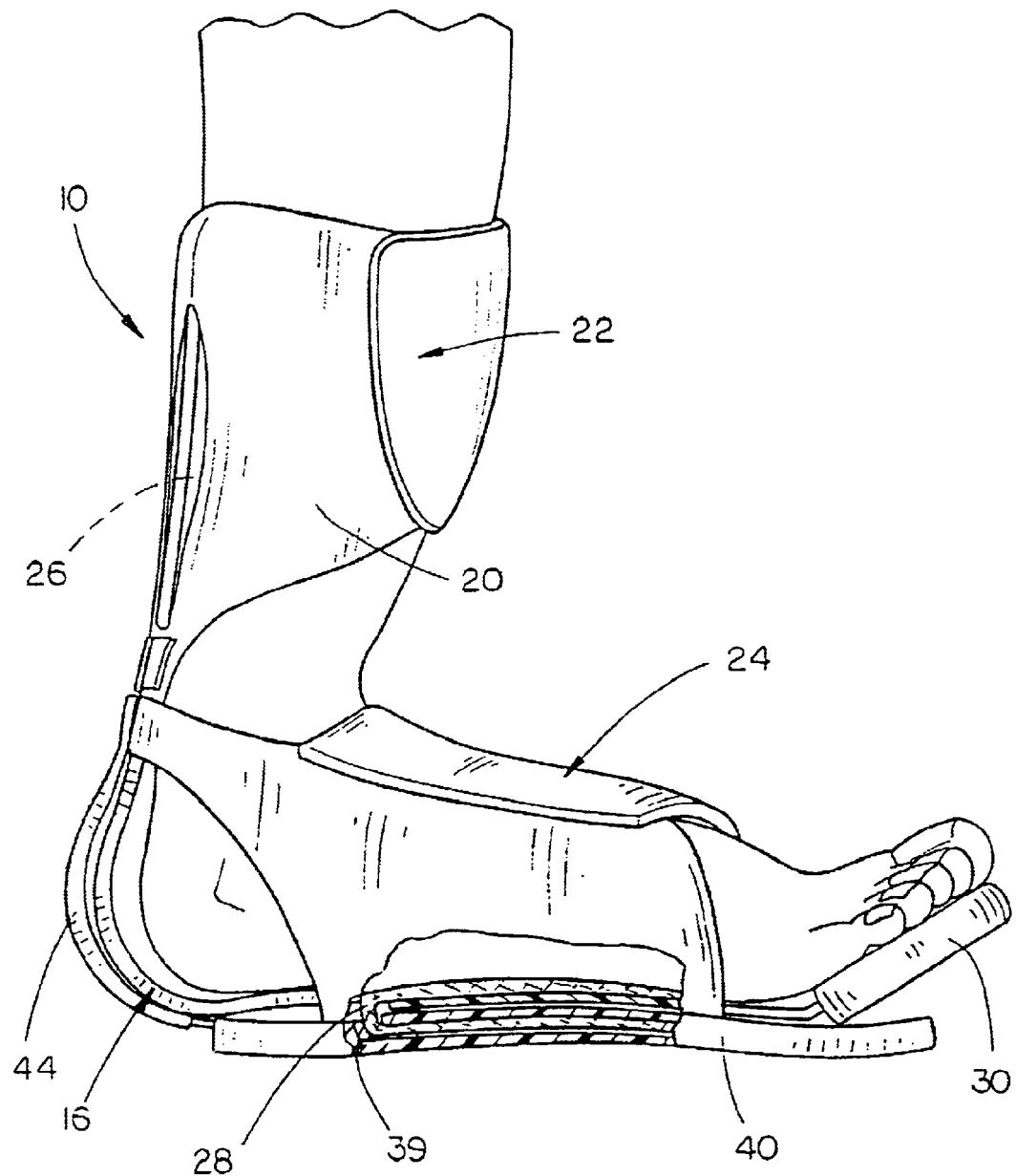
FIG. 2 is a side elevational view of the foot orthosis of the present invention.
Figure 3:
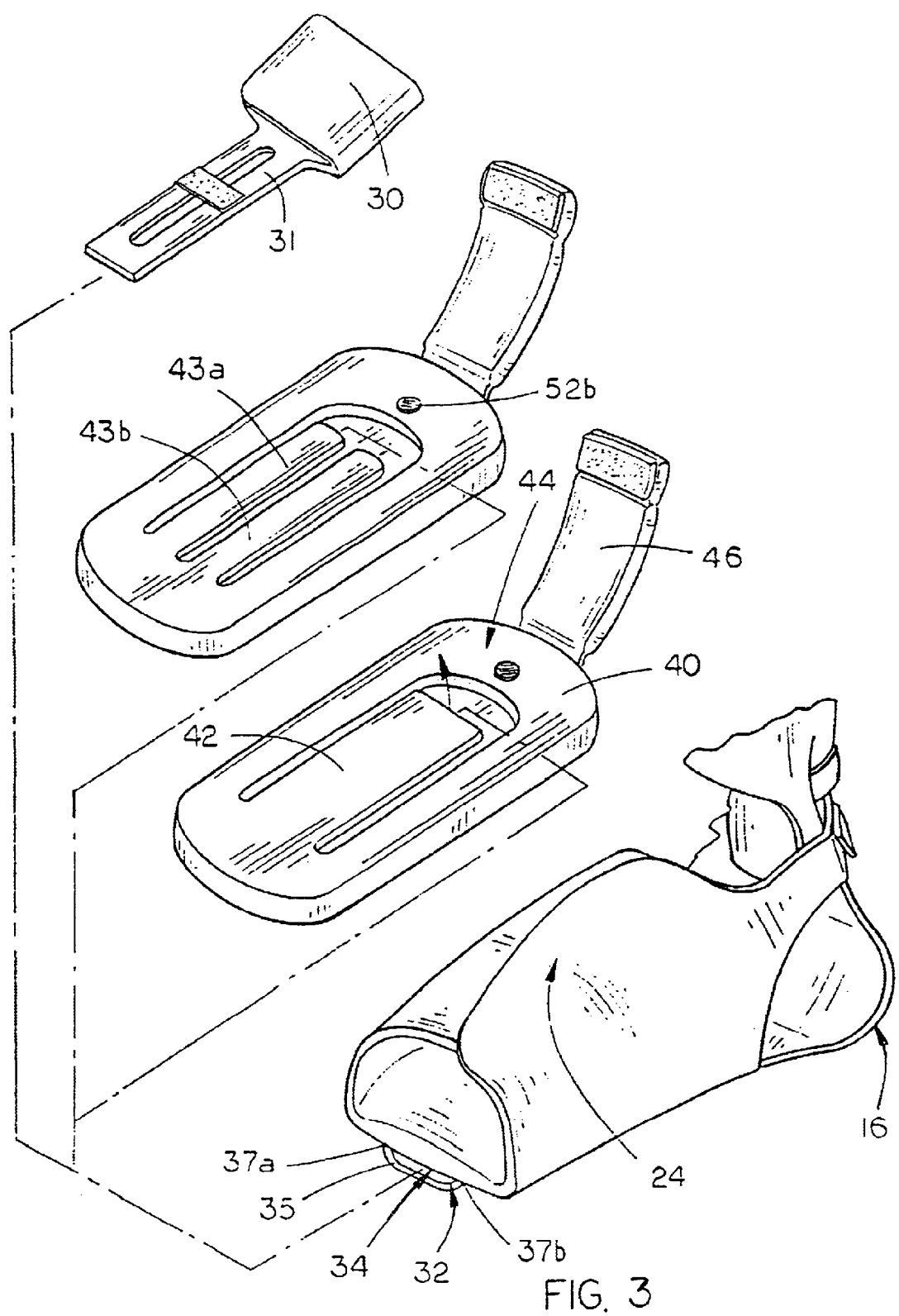
FIG. 3 is a detailed exploded perspective view showing the attachment of the skid pad and toe plate to the boot.

The foot orthosis 10 of the present invention includes an L-shaped semi-flexible splint 12 having an extended leg-engaging section 14, a relatively wide heel portion 16, a forwardly extending foot support section 18 and an anti-rotation bar 19 to prevent lower extremity rotation, as shown best in FIGS. 1–3. Preferably, the L-shaped splint 12 would be constructed of a transparent PVC plastic such as Cleardex™ or KYDEX™ having a small degree of flexibility to permit minor motion of the leg and foot. It has been found that the plastic thickness should be between ⅛" and ½", although the thickness is not critical to the present invention. The benefits of the transparent material being used will be detailed later in this disclosure.

A fabric boot 20 is fitted on and removably mounted to the L-shaped splint 12 and would preferably include leg and foot access flaps 22 and 24 to permit the foot orthosis 10 to be fitted onto the leg and foot of the wearer of the foot orthosis 10, as shown in FIG. 2. In the preferred embodiment, the boot 20 would be constructed of a washable polyester tricot fabric or the like, although the exact material used is not critical so long as the securement characteristics of the boot 20 are maintained. It is further preferred that the leg access flap 22 and the foot access flap 24 be releasably securable by hook and loop securement devices or the like to receive and comfortably retain the leg and foot of the wearer there within, and further that the unit include padding to protect sensitive injured parts of the patient from further damage.

As shown best in FIGS. 1 and 2, the heel portion of fabric boot 20 is open to permit viewing of the heel within the foot orthosis 10 and thereby facilitate diagnosis of the foot condition of the patient. The transparent nature of the L-shaped splint 12 further facilitates the viewing of the heel of the patient through the foot orthosis 10 without mandating removal of the foot orthosis 10 to conduct such inspection. It thus becomes far easier for doctors, nurses and other staff to inspect the heel of the patient wearing the foot orthosis 10 and thus confirm that degradation of the heel is not taking place due to extended periods of bed rest or the like. The design of the L-shaped splint 12 is such that the patient's heel is "floated" to virtually eliminate heel contact with a resting surface, which is a common cause of bed sores for bed ridden patients.

Additional features found in the present invention would include an Achilles support pad 26 mounted on the boot 20 adjacent the leg support portion 14 of the L-shaped splint 12 which provides additional padding for the Achilles tendon of the patient, which is particularly important when the patient is recumbent for extended periods of time. Additionally, a foot pad 28 is provided on the fabric boot 20 adjacent foot support section 18 to permit the heel of the patient to "float" during walking, which is particularly important for those patients with decubitus or other such bone and tendon degradation maladies caused by long periods of bed rest.

It is to be understood that many of the above described elements of the present invention are generally found in the prior art, are generally conventional and do not in and of themselves comprise the inventive elements of the present invention. However, one of the problems found in foot orthotic devices of the prior art which is not addressed is that to attach or remove elements to the foot section 18 of the L-shaped splint 12 requires the use of a nut and bolt arrangement, such as that shown in Varn, U.S. Pat. No. 5,569,173. This means that the majority of prior art devices include a screw mounted on the underside of the foot section of the splint, which is generally regarded as invasive hardware and can potentially result in injury to the patient due to the location of the screw on the orthotic device. Furthermore, as the toe plate 30 is commonly secured to the L-shaped splint 12 by the same nut and bolt combination, removal of and adjustment of the toe plate 30 mandates adjustment of the nut and bolt combination, further risking injury to the patient wearing the orthotic device due to the twisting and turning of the nut and bolt.

Figure 4:
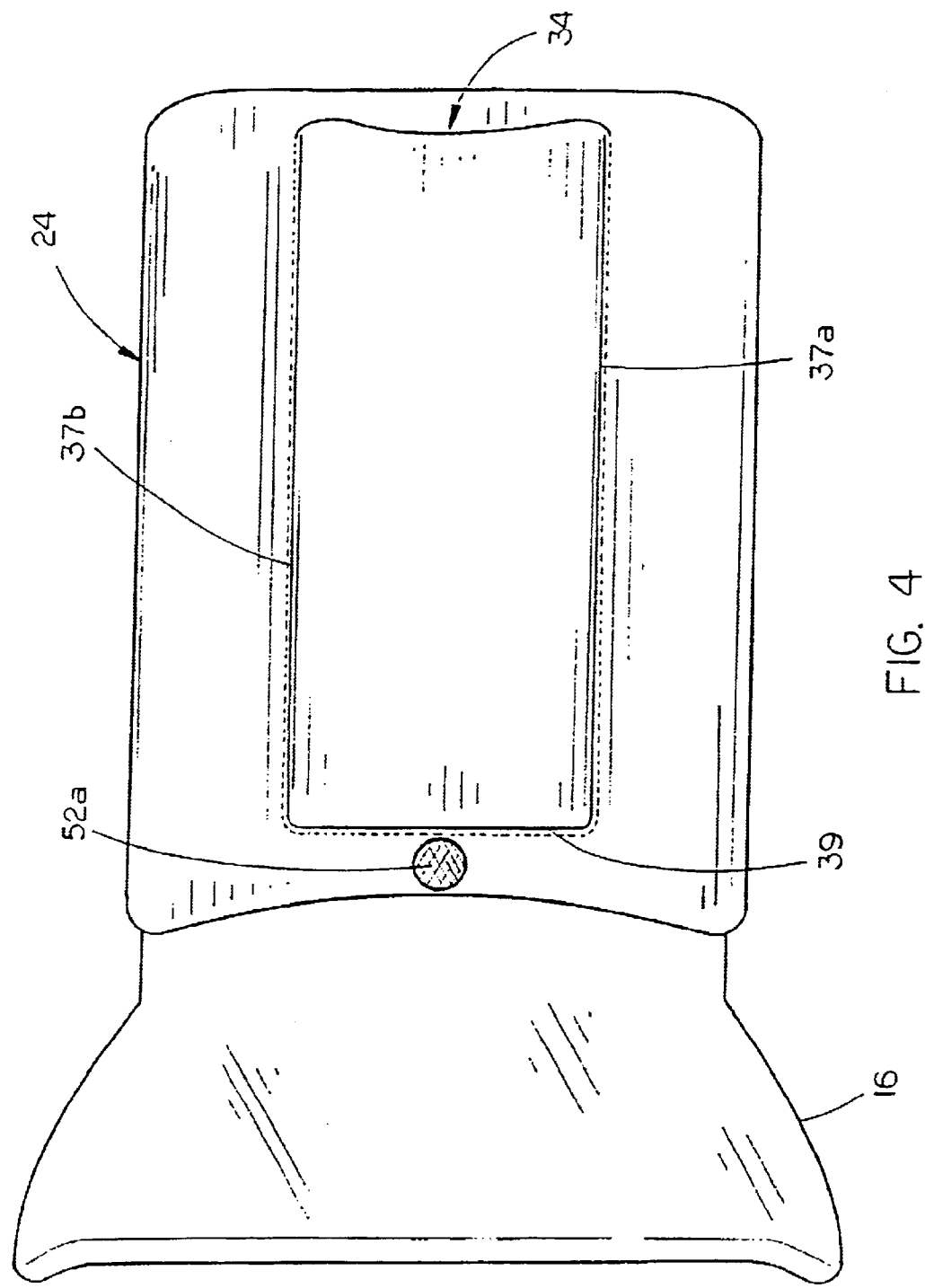
FIG. 4 is a bottom plan view showing the pocket.

The present invention substantially eliminates the dangers inherent in the prior art caused by the nut and bolt combination by inventing and including the following functional features. The skid pad 40 is preferably a rounded generally rectangular pad of closed cell expanded vinyl, the skid pad 40 including a tongue portion 42 mounted on the upper surface 44 of the skid pad 40, as shown best in FIGS. 2 and 3. It is preferred that the construction material used in connection with the skid pad 40 be extremely durable such that the skid pad 40 and tongue 42 have an extended usable lifespan, which is superior to those devices found in the prior art. The skid pad 40 may also include a layer of textured rubber to keep the skid from slipping, although it may be of any type of appropriate non-skid material. Preferably, the tongue 42 consists of a cut out section of skid pad 40 which is separated from skid pad 40 along the longitudinal length thereof and remains attached at the forward end thereof to permit the tongue 42 to be pivoted upwards from the skid pad 40. Mounted on the underside of fabric boot 20 is a tongue-receiving pocket 32, which is generally rectangular in shape and extends longitudinally along the underside of fabric boot 20 and includes a forward opening 34. The pocket 32 includes an outer wall 35 which is generally semi-cylindrical in shape and has left and right longitudinal edges 37a and 37b which are each connected to the underside of the fabric boot 20 thus leaving a tongue-receiving cavity having a forward opening 34 for receiving the tongue 42 therein. The rear edge 39 of the outer wall 35 is likewise connected to the underside of fabric boot 20 thus creating the tongue-receiving pocket 32 as shown in FIGS. 3 and 4. In the preferred embodiment, tongue 42 of skid pad 40 would be slid into forward opening 34 of tongue-receiving pocket 32 until tongue 42 is securely seated within the tongue-retaining section of tongue-receiving pocket 32, as shown best in FIG. 2. Because pocket 32 is only slightly larger than tongue 42, there is substantial frictional contact between tongue 42 and the interior of the tongue-receiving pocket 32 which prevents the tongue 42 from sliding out of tongue-receiving pocket 32 absent intentional force being applied to remove tongue 42 from tongue-receiving pocket 32. No other bottom-mounted securement means is necessary to secure tongue 42 within tongue-receiving pocket 32 and thus it is seen that the intrusive hardware found in the prior art is eliminated by the present invention. However, to insure that the skid pad 40 stays on the foot orthosis 10, a strap 46 is connected to the skid pad 40 and extends rearwardly therefrom for connection to the boot 20 at a position behind and above the skid pad 40. The strap 46 would preferably include a section of hook and loop securement fabric mounted on the rearward end thereof for attachment to the boot 20, the attachment shown best in FIGS. 1 and 2.

Although it is preferred that the tongue 42 and tongue-receiving pocket 32 utilize only frictional securement to secure the tongue therein, it has been found that for those patients that are more ambulatory than average, it is sometimes desirable to enhance the frictional securement of the tongue 42 within the tongue-receiving pocket 32 by including a supplemental fastening device such as a fabric-type fastening device mounted on the underside of the fabric boot 20 immediately rearward of the tongue-receiving pocket 32, as shown best in FIGS. 3 and 4. This fastening device would consist of two separatable mating sections, one section 52a mounted on the fabric boot 20 and the other section 52b mounted on the upper surface of the skid pad 40. While various types of fastening devices may be used with the present invention, such as hook and loop fasteners and the like, in the preferred embodiment, a fastener manufactured by 3M of Minnesota has been found to provide excellent securement while being generally non-invasive. The fastener is marketed under the name "3M Dual Lock Reclosable Fastener" and consists of hundreds of mushroom-shaped stems which interlock with one another, producing an audible "snap" which announces that the fastener is locked. Of course, various other types of fasteners can be used with the present invention, although it has been found that this type of fastening device provides secure and safe fastening of the skid pad 40 to the fabric boot 20.

Additionally, the toe plate 30 is secured on the L-shaped splint 12 by a rearward extending tongue portion 31 which fits within and is releasably secured in tongue-receiving pocket 32 by a small strip of hook and loop fastening fabric or the like which may be mounted on the tongue portion 31 or in the pocket 32. In this manner, the toe plate 30 may be positioned forwards or rearwards relative to the foot support section 18 of L-shaped splint 12 by merely sliding the toe plate in and out of the tongue-receiving pocket 32. When the toe plate 30 is in its desired position, the small strip of hook and loop fastener will be secured to the interior wall of tongue-receiving pocket 32 and the toe plate 30 would thus be releasably secured in the desired position.

It is thus seen that the skid pad 40 and toe plate 30 may be quickly and easily removed from the foot orthosis 10 of the present invention without requiring the patient to lift or move his or her foot or requiring the staff person to unscrew a nut to access the skid pad 40 or toe plate 30. Many of the potential problems involved in staff-patient contact are thus eliminated, rendering the present invention far superior to those devices found in the prior art. The ease of removal and attachment of the skid pad 40 and toe plate 30 are especially important with patients who are ambulatory and thus require the addition or removal of those elements several times during the day.

One modification that should be noted is that it may be beneficial to include more than one tongue-receiving pocket which will interact with multiple skid pad tongues 43a and 43b, as shown in FIG. 3, in order to provide additional frictional securement for the skid pad 40 on the boot 20. To that end, it should be noted that the precise number, size and shape of the pockets is not critical to the invention so long as the functional characteristics of the invention are maintained, specifically that the pocket receive and releasably retain the tongue.

It is to be understood that numerous modifications, additions and substitutions may be made to the foot orthosis of the present invention which fall within the intended broad disclosure. For example, the construction materials used in the present invention may be modified and or changed so long as the functional characteristics of the present invention are maintained. Also, the precise size, shape and nature of the tongue 42 and tongue-receiving pocket 32 may be modified so long as the functional characteristics of the pocket are maintained, specifically the ease of removability and retention of skid pad 40. Finally, the size and shape of the invention may be modified so long as the functional characteristics are not destroyed or greatly modified.

There has thus been shown and described a foot orthotic device which accomplishes at least all of the intended objectives.

We claim:

1. A foot orthosis comprising;
a generally "L"-shaped splint having a generally upright leg-engaging section and a forwardly-extending foot support section;
a generally flexible foot receiving and retaining boot mounted on said splint for releasably securing a foot on said splint;
a tongue-receiving pocket mounted on one of said splint and said boot, said tongue-receiving pocket having at least one opening and a tongue retaining section;
a generally planar skid pad including an attached tongue section projecting from said skid pad; and
said tongue section of said skid pad being insertable into said tongue-receiving pocket such that said tongue is releasably secured in said tongue-receiving pocket and said skid pad is releasably secured on one of said splint and said boot.

2. The foot orthosis of claim 1 further comprising a forwardly extending toe plate which includes a forward toe support plate and a rearwardly extending tongue portion which fits within and is releasably secured in said tongue-receiving pocket such that said toe plate may be positioned forwards or rearwards relative to said foot support section of said L-shaped splint by sliding said tongue portion of said toe plate into and out of said tongue-receiving pocket.

3. The foot orthosis of claim 1 wherein said generally "L"-shaped splint is constructed of a semi-flexible, generally transparent PVC plastic such that the healing status of the foot is viewable without requiring removal of said splint.

4. The foot orthosis of claim 1 wherein said boot further comprises a leg access flap and a foot access flap each operative to allow a respective leg and foot to be inserted into said boot, said boot being constructed of a fabric material and said leg access flap and said foot access flap each further comprising securement means for releasably securing a leg and foot within said boot by at least one hook and loop securement device.

5. The foot orthosis of claim 1 wherein said tongue-receiving pocket comprises a longitudinally extended generally semi-cylindrical curved outer wall having left and right longitudinal edges and a rear edge, said outer wall mounted on the underside of said boot with said left and right longitudinal edges and said rear edge connected to said boot, said curved outer wall and said boot thereby forming said tongue-receiving pocket having one opening for receiving and releasably retaining said tongue therein.

6. The foot orthosis of claim 1 wherein said tongue of said skid pad comprises a cut out section of said skid pad which is separated from said skid pad along the longitudinal length thereof and remains attached at the forward end thereof thereby permitting said tongue to be pivoted upwards from said skid pad for insertion into said tongue-receiving pocket.

7. The foot orthosis of claim 1 further comprising at least two tongue-receiving pockets.

8. A foot orthosis comprising;
a generally "L"-shaped splint having a generally upright leg-engaging section and a forwardly-extending foot support section;
a generally flexible foot receiving and retaining boot mounted on said splint for releasably securing a foot on said splint;
a tongue-receiving pocket mounted on one of said splint and said boot, said tongue-receiving pocket having at least one opening and a tongue retaining section;
a generally planar skid pad including an attached tongue section projecting from said skid pad;

a forwardly extending toe plate which includes a forward toe support plate and a rearwardly extending tongue portion; and said tongue section of said skid pad and said tongue portion of said toe plate each being insertable into said tongue-receiving pocket such that said tongue section of said skid pad and said tongue portion of said toe plate are each releasably secured in said tongue-receiving pocket and said skid pad and said toe plate are releasably secured on one of said splint and said boot.

9. The foot orthosis of claim 8 wherein said generally "L"-shaped splint is constructed of a semi-flexible, generally transparent PVC plastic such that the healing status of the foot is viewable without requiring removal of said splint.

10. The foot orthosis of claim 8 wherein said boot further comprises a leg access flap and a foot access flap each operative to allow a respective leg and foot to be inserted into said boot, said boot being constructed of a fabric material and said leg access flap and said foot access flap each further comprising securement means for releasably securing a leg and foot within said boot by at least one hook and loop securement device.

11. The foot orthosis of claim 8 wherein said tongue-receiving pocket comprises a longitudinally extended generally semi-cylindrical curved outer wall having left and right longitudinal edges and a rear edge, said outer wall mounted on the underside of said boot with said left and right longitudinal edges and said rear edge connected to said boot, said curved outer wall and said boot thereby forming said tongue-receiving pocket having one opening for receiving and releasably retaining said tongue therein.

12. The foot orthosis of claim 8 wherein said tongue of said skid pad comprises a cut out section of said skid pad which is separated from said skid pad along the longitudinal length thereof and remains attached at the forward end thereof thereby permitting said tongue to be pivoted upwards from said skid pad for insertion into said tongue-receiving pocket.

13. The foot orthosis of claim 8 further comprising at least two tongue-receiving pockets.

14. A foot orthosis comprising;
a splint for supporting a human foot;
a foot receiving and retaining boot mounted on said splint for releasably securing a foot on said splint;
a tongue-receiving pocket mounted on one of said splint and said boot, said tongue-receiving pocket having at least one opening and a tongue retaining section;
a skid pad including a projecting tongue section; and
said tongue section of said skid pad being insertable into said tongue-receiving pocket such that said tongue is releasably secured in said tongue-receiving pocket and said skid pad is releasably secured on one of said splint and said boot.

15. The foot orthosis of claim 14 wherein said tongue section of said skid pad is frictionally secured within said tongue-receiving pocket.

16. The foot orthosis of claim 15 wherein said tongue section of said skid pad is additionally releasably secured within said tongue-receiving pocket by a supplemental fastening means.

* * * * *